United States Patent [19]

Stark

[11] 4,344,887
[45] Aug. 17, 1982

[54] METHOD FOR EPOXIDIZING OLEFINS

[75] Inventor: Charles J. Stark, Clifton Park, N.Y.

[73] Assignee: General Electric Company, Schenectady, N.Y.

[21] Appl. No.: 263,839

[22] Filed: May 15, 1981

Related U.S. Application Data

[63] Continuation-in-part of Ser. No. 107,899, Dec. 28, 1979, abandoned.

[51] Int. Cl.$^3$ ............................................. C07D 301/12
[52] U.S. Cl. ..................................................... 549/531
[58] Field of Search .................................... 260/348.31

[56] References Cited

U.S. PATENT DOCUMENTS 3,518,285  6/1970  Fenton et al. .................. 260/348.31

FOREIGN PATENT DOCUMENTS 2132965  1/1972  Fed. Rep. of Germany ........................ 260/348.31
2803791  8/1978  Fed. Rep. of Germany .
2423486  11/1979  France .
 868890  5/1961  United Kingdom ........... 260/348.27
1399639  7/1975  United Kingdom .

OTHER PUBLICATIONS

Chemical Abstracts, vol. 89, (1978), 59832p.
Richard P. Heggs et al, Jour. Am. Chem. Soc., vol. 101:9, Apr. 25, 1979, pp. 2484–2486.

*Primary Examiner*—Norma S. Milestone
*Attorney, Agent, or Firm*—William A. Teoli; James C. Davis, Jr.

[57] ABSTRACT

A mixture of tetrachloroacetone and hydrogen peroxide has been found effective for epoxidizing olefinically unsaturated organic material dissolved in various aromatic or halogenated aliphatic organic solvents.

4 Claims, No Drawings

METHOD FOR EPOXIDIZING OLEFINS

CROSS REFERENCE TO RELATED APPLICATIONS

This application is a continuation-in-part of my copending application Ser. No. 107,899, filed Dec. 28, 1979 now abandoned, which is assigned to the same assignee as the present invention.

BACKGROUND OF THE INVENTION

Prior to the present invention, attempts to epoxidize olefinically unsaturated organic materials with hydrogen peroxide have met with only limited success. One procedure, is shown by U.S. Pat. No. 2,786,854, based on the use of an inorganic peracid, such as a peracid of tungsten, which proved to be inactive with olefinically unsaturated hydrocarbons. Another procedure is shown by British Pat. No. 1,399,639, directed to a process for epoxidizing olefinically unsaturated compounds with hydrogen peroxide in the presence of a fluorinated ketone and/or fluorinated ketone hydrate. Although improved results were achieved with the use of fluorinated ketones as a catalyst, it was often difficult to obtain fluorinated ketone such as hexafluoroacetone commercially. As a result, the feasibility of employing such catalysts for the hydrogen peroxide epoxidation of olefinically unsaturated organic materials was economically unattractive.

The present invention is based on the discovery that tetrachloroacetone, an inexpensive, commercially available material can be utilized with hydrogen peroxide to effect the epoxidation of a variety of olefinically unsaturated organic materials if utilized in a particular manner in the presence of an inert organic solvent. One procedure, for example, involves the employment of a buffer, such as sodium hydrogen phosphate when utilizing the tetrachloroacetone and the olefinically unsaturated organic material in the presence of an effective amount of the hydrogen peroxide. Another procedure involves the incremental addition of the hydrogen peroxide to the tetrachloroacetone-olefinically unsaturated organic material reaction mixture while it is refluxing. It has been found that the tetrachloroacetone can be recovered and recycled after the epoxidation of the olefinically unsaturated organic material.

STATEMENT OF THE INVENTION

One form of the invention is directed to an epoxidation method which comprises,
 (1) effecting reaction between an olefinically unsaturated organic material and an aqueous 30–90% by weight hydrogen peroxide solution in the presence of symmetrical tetrachloroacetone, an inert organic solvent and a buffer, where there is used at least 1 mole of tetrachloroacetone per site of olefinic unsaturation in the olefinically unsaturated organic material,
 (2) combining the resulting mixture of (1) with an inert $C_{(5-8)}$ aliphatic hydrocarbon solvent,
 (3) separating the organic layer from the mixture of (2),
 (4) washing the recovered organic layer with an aqueous base solution and
 (5) distilling the washed organic layer to effect recovery of the epoxidized organic material from (4).

Another aspect of the present invention is directed to an epoxidation method which comprises
 (1) incrementally adding aqueous 30–90% by weight hydrogen peroxide to a refluxing mixture comprising an olefinically unsaturated organic material, symmetrical tetrachloroacetone, and an inert organic solvent,
 (2) continuously azeotroping water of reaction from the mixture of (1) until the mixture is substantially free of water,
 (3) washing the resulting organic solution of (2) with an aqueous base and
 (4) distilling the inert organic solvent from the resulting solution of (3) to effect recovery of the epoxidized organic material.

Olefinically unsaturated organic materials which can be epoxidized in accordance with the practice of the present invention include any olefin or polyolefin having a molecular weight in the range of between 56–2,000 which is soluble in $C_{(6-13)}$ aromatic hydrocarbons and halogenated aromatic hydrocarbons, and $C_{(1-12)}$ halogenated aliphatic hydrocarbons and which have one or more sites of olefinic unsaturation corresponding to the formula,

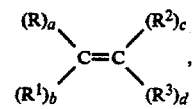

where R, $R^1$, $R^2$ and $R^3$ can be hydrogen, or a $C_{(1-13)}$ monovalent hydrocarbon radical, and where up to 2 of the R, $R^1$, $R^2$ and $R^3$ radicals can be hydrogen, and a, b, c and d can be 0 or 1 and the sum of $a+b+c+d$ can be equal to 2–4 inclusive.

Among the preferred olefinically unsaturated organic materials which can be epoxidized in the practice of the invention are acyclic olefins having a molecular weight of at least 56. Other olefinically unsaturated organic materials which can be utilized in the practice of the invention are $C_5$–$C_8$ cycloaliphatic organic compounds having one or two sites of olefinic unsaturation.

Additional olefinically unsaturated organic materials which can be utilized in the practice of the present invention include, for example, allyl ethers, mono and poly $C_{(3-22)}$ glycerides having one or more sites of olefinic unsaturation as previously defined. Some of these olefinically unsaturated materials are as follows:

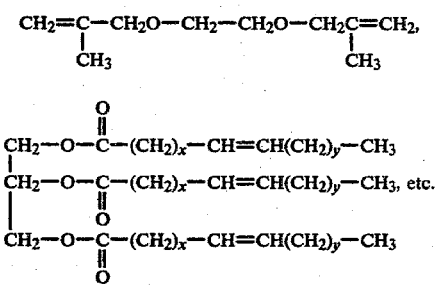

Further examples of epoxidizable olefins which can be used in the practice of the invention are, for example,

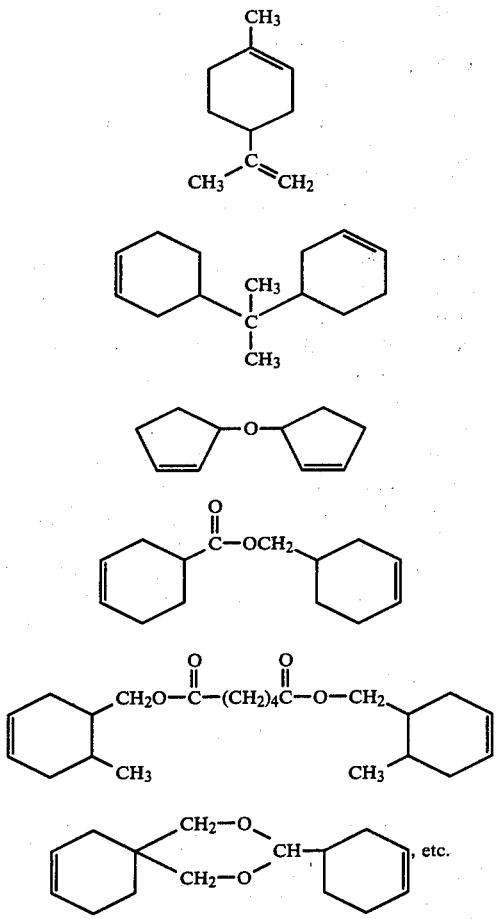

Additional olefins can be found in the Handbook of Epoxy Resins, by Henry Lee and Kris Neville, McGraw-Hill, 1967.

Among the aromatic hydrocarbon solvents which can be used in the practice of the present invention are, for example, benzene, toluene, mesitylene, ethylbenzene, o-xylene, p-xylene, butylbenzene, etc.; halogenated aromatic hydrocarbons which are included are, for example, chlorobenzene, o-dichlorobenzene, p-dichlorobenzene, bromobenzene, etc.; halogenated aliphatic hydrocarbon solvents which can be used are, for example, chloroform, dichloromethane, 1,1,2,2-tetrachloroethane, 1,1,2,2-tetrabromoethane, 1,1,2,2-tetrachloro-difluoroethane, 1,2-dichloroethane, 1,1,1-trichloroethane, etc.

In addition to the above-described aromatic hydrocarbon solvents, halogenated aromatic hydrocarbon solvents and halogenated aliphatic solvents, there also can be used in the practice of the invention to facilitate the recovery of the epoxidized organic material, inert $C_{(5-8)}$ hydrocarbon solvents, for example, pentane, hexane, heptane and octane.

In the practice of the invention, olefin epoxidation can be accomplished by either the buffer method, based on the presence of substantially equivalent amounts of the tetrachloroacetone and olefinic unsaturation in the reaction mixture or the catalytic method where less than an equivalent amount of the tetrachloroacetone per equivalent of olefinic unsaturation can be used. It is preferred to utilize at least one mole of the tetrachloroacetone per mole of olefinic unsaturation in the olefinically unsaturated organic material. Additional amounts of buffer can be used at higher levels of tetrachloroacetone usage.

Further distinction between the buffer method and the catalytic method is that the buffer method can be practiced at ambient conditions, while the catalytic method is generally practiced under reflux conditions. There can be utilized in the buffer method and the catalytic method, a ratio of from about 1 to about 10 moles of hydrogen peroxide and preferably 1.5 moles to 2 moles of hydrogen peroxide, per mole of the tetrachloroacetone. In the catalytic method, the hydrogen peroxide can be added incrementally to the reaction mixture while it is refluxing to provide for the separation of water based on the formation of an azeotrope. In the catalytic method, the mole ratio of tetrachloroacetone to olefin can vary from 0.5 to 0.85 moles of tetrachloroacetone per mole of olefinic unsaturation in the epoxidation method mixture.

Buffers which can be used in the buffer method can include alkali metal phosphates, alkali metal hydrogen phosphates, alkali metal carbonates, alkali metal bicarbonates. Some of the buffers which can be utilized are, for example, sodium dihydrogenphosphate, sodium pyrophosphate, sodium citrate, sodium perborate, sodium borate, sodium tartrate and the corresponding potassium salts. There can be used from 0.1 to 0.5 moles of buffer per mole of the tetrachloroacetone.

Bases which can be utilized to wash the recovered organic layer to effect removal of tetrachloroacetone in the form of an aqueous solution are, for example, alkali metal hydroxides, such as sodium hydroxide, potassium hydroxide, etc.; alkali metal carbonates and bicarbonates, for example, sodium carbonate, potassium carbonate, sodium bicarbonate, etc. There can be used at a least an amount of base which is at least equivalent to the moles of tetrachloroacetone in the recovered organic layer to provide effective results.

In order that those skilled in the art will be better able to practice the invention, the following examples are given by way of illustration and not by way of limitation. All parts are by weight.

EXAMPLE 1

There was added 2.34 parts of 2-methyl-1-hexene to a mixture which was being stirred consisting of 9.41 parts of tetrachloroacetone, 5 parts of a 50% aqueous hydrogen peroxide, 7.5 parts of chloroform and 0.86 part of disodium hydrogen phosphate. The resulting mixture was stirred for 16 hours at ambient temperatures and then an additional 1.68 parts of 50% aqueous hydrogen peroxide was added. After 24 hours, the mixture was poured into 19 parts of pentane and the aqueous layer removed. The organic layer was washed with three 50 part portions of water and then stirred for 10 minutes with 30–40 parts of a 6-N-sodium hydroxide aqueous solution. The organic phase was next washed with saturated sodium bisulfite, dried with magnesium sulfate and then diluted. Based on vapor phase chromatographic analysis, there was obtained an 81% yield of 2-methyl-1-hexene oxide. Only a trace of olefin was detected. Upon distillation of the remaining organic phase through a Vigreaux column, there was obtained four fractions. Fraction four provided a yield of 53% of 2-methyl-1-hexene oxide. The identity of the product was confirmed by IR, $^1$H NMR, $^{13}$C NMR.

EXAMPLE 2

The procedure of Example 1 was repeated, except that in place of 2-methyl-1-hexene there was employed cyclohexene. In addition, a variety of halogenated carbonyl compounds were evaluated with cyclohexene as hydrogen peroxide epoxidation catalysts. The following results were obtained:

TABLE I

| Chlorinated Carbonyl | Cyclohexene % Recovery | Cyclohexene Oxide Yield |
| --- | --- | --- |
| $Cl_3C-\overset{O}{\underset{\|\|}{C}}-CCl_3$ | 69 | 18 |
| $Cl_3C-\overset{O}{\underset{\|\|}{C}}-CHCl_2$ | 76 | 16 |
| $Cl_2CH-\overset{O}{\underset{\|\|}{C}}-CHCl_2$ | 7 | 78 |
| $ClCH_2-\overset{O}{\underset{\|\|}{C}}-CHCl_2$ | 83 | 7 |
| $Cl_3C-\overset{O}{\underset{\|\|}{C}}-H$ | 40 | 17 |
| $C_6H_5-\overset{O}{\underset{\|\|}{C}}-CHCl_2$ | 87 | 0 |

The above results show that the tetrachloroacetone of the present invention provides unexpectedly better yields of the cyclohexene oxide than closely related chlorinated carbonyl compounds when used as a hydrogen peroxide catalyst for the epoxidation of cyclohexene.

EXAMPLE 3

The procedure of Example 1 was repeated, except that there was utilized 2 moles of hydrogen peroxide, per mole of tetrachloroacetone. In addition, a variety of olefins were epoxidized in accordance with the practice of the present invention. The respective epoxidation mixtures were then evaluated by vapor phase chromatography to determine the yield of the epoxide and the percent of unreacted olefin. In addition, the epoxides were recovered in accordance with the procedure of Example 1, "% Epoxide Isolated". The results obtained are shown in Table II.

TABLE II

| Olefin | Epoxide % Yield By VPC | Olefin % Recovery (VPC) | Epoxide % Isolated |
| --- | --- | --- | --- |
| cyclohexene | 75 | trace | 55 |
| (CH₃)₂C=CH(CH₃) | trace | 57 | |
| (CH₃)₂C=C(CH₃)H | 80 | 5 | 57 |
| cycloheptenol (OH) | 93 (>99% cis) | — | 51 |

The above results show that the epoxidation method of the present invention can be used to epoxidize a wide variety of olefins.

EXAMPLE 4

There were added 13.68 parts of a 50% aqueous hydrogen peroxide to a refluxing mixture of 3.92 parts of tetrachloroacetone, 11.58 parts of cyclooctene and 149 parts of chloroform. Water was removed continuously as it was formed, over a period of 4 hours of heating. The removed water was then added to the reaction mixture. The organic phase was then separated from the aqueous phase. Based on VPC analysis there was obtained an 83% yield of cyclooctene oxide.

Based on the above results, the method of the present invention also includes a "catalytic" procedure which does not require equal molar amounts of tetrachloroacetone and the olefin, or the use of a buffer. In addition, a major amount of the tetrachloroacetone can be obtained from the water washings resulting from the workup of the reaction mixture. The washings were heated to 50°–60° C. under vacuum to facilitate the evaporation of the excess water. The residual water can then be removed by azeotropic distillation, followed by the removal of the remaining hexane. There was obtained up to 70% of the tetrachloroacetone used in the original reaction mixture.

Although the above examples are directed to only a few of the very many variables of the method of the present invention, it should be understood that the present invention is directed to an epoxidation method utilizing tetrachloroacetone and an olefin, in combination with hydrogen peroxide and organic solvent, as shown in the description preceding these examples.

What I claim as new and desire to secure by Letters Patent of the United States is:

1. An epoxidation method which comprises,
   (1) effecting reaction between an olefinically unsaturated organic material and an aqueous 30–90% by weight hydrogen peroxide solution in the presence of symmetrical tetrachloroacetone, an inert organic solvent and a buffer, where there is used at least 1 mole of tetrachloroacetone per site of olefinic unsaturation in the olefinically unsaturated organic material,
   (2) combining the resulting mixture of (1) with an inert $C_{(5-8)}$ aliphatic hydrocarbon solvent,
   (3) separating the organic layer from the mixture of (2),
   (4) washing the recovered organic layer with an aqueous base solution and
   (5) distilling the washed organic layer to effect recovery of the epoxidized organic material from (3).

2. A method in accordance with claim 1, where the inert organic solvent is chloroform.

3. A method in accordance with claim 1, where the buffer is disodium hydrogen phosphate.

4. A method in accordance with claim 1, where the olefinically unsaturated material is 2-methyl-1-hexene.

* * * * *